(12) United States Patent
Yakabe et al.

(10) Patent No.: US 6,472,011 B1
(45) Date of Patent: Oct. 29, 2002

(54) L-CARNITINE AGENT

(75) Inventors: Takafumi Yakabe, Tsurugashima; Kiyoko Ozaki, Kariya; Masaharu Shimatani, Sayama; Tadashi Idota, Kawagoe, all of (JP)

(73) Assignee: Snow Brand Milk Products Co., Ltd., Hokkai-do (JP)

( * ) Notice: Subject to any disclaimer, the term of this patent is extended or adjusted under 35 U.S.C. 154(b) by 0 days.

(21) Appl. No.: 09/923,849

(22) Filed: Aug. 7, 2001

Related U.S. Application Data

(62) Division of application No. 09/467,149, filed on Dec. 19, 1999, now abandoned.

(30) Foreign Application Priority Data

Jan. 13, 1999 (JP) ............................................ 11-006729

(51) Int. Cl.$^7$ ........................... A61K 31/14; A61K 9/14; A23C 19/00
(52) U.S. Cl. ........................ 426/583; 514/642; 424/489
(58) Field of Search .................. 426/583; 424/489; 514/642

(56) References Cited

U.S. PATENT DOCUMENTS 5,436,020 A   7/1995   Kuwata et al.

FOREIGN PATENT DOCUMENTS

| CN | 1 107 656 | 9/1995 |
| JP | 62 063553 | 3/1987 |

*Primary Examiner*—Theodore J. Criares
*Assistant Examiner*—Jennifer Kim
(74) *Attorney, Agent, or Firm*—Knobbe, Martens, Olson & Bear, LLP

(57) ABSTRACT

An L-carnitine agent has an indispensable function in the body and utility as a material for pharmaceutical agents or food and drink. By subjecting milk or modified milk products of mammals from which casein is removed, to the treatment of desalting and partial removal of lactose followed by drying, L-carnitine content, lactose content, and ash content are adjusted to 0.1~100 mmol/100 g, 20~95 g/100 g, and 5 g/100 g or less, respectively.

7 Claims, No Drawings

L-CARNITINE AGENT

This application is a divisional of prior application Ser. No. 09/467,149, filed Dec. 19, 1999, now abandoned. The complete disclosure of this previous application is hereby incorporated by reference.

BACKGROUND OF THE INVENTION

1. Field of the Invention

The present invention relates to an L-carnitine agent and a method for producing thereof, wherein the starting material is milk or modified milk products of mammals. The L-carnitine agent of the present invention is characterized by features including simple handling, use of milk or modified milk products of mammals as a starting material, the absence of toxic D-carnitine, and thus superior safety.

2. Description of the Related Art

L-carnitine is a water-soluble compound which easily forms fatty-acids and ester via alcohol residue in the molecules, and is also referred to as Vitamin BT. Major function of L-carnitine in the body is the oxidation of fatty acids in mitochondria. Upon acting as a shuttle, L-carnitine transports fatty acids into and out of mitochondria via mitochondrial membrane. Thus, L-carnitine is an indispensable component for energy production in the body.

L-carnitine is biologically synthesized from lysine and methionine in the body. However, only 25% of the total metabolic turnover of L-carnitine is endogenously synthesized in the body. Therefore, the remaining 75% metabolic turnover is derived from food. Although the amount of endogenous L-carnitine is normally reported to be sufficient for older children or adults, it is observed that hypercatabolism of fat is enhanced at time of fasting even for healthy children, consequently increasing acyl CoA, and resulting in the increase of esterified L-carnitine. For pediatric patients with organic acidemia, for example, propionicacidemia or methylmalonicacidemia, the level of acyl-L-carnitine such as propionyl-L-carnitine is increased. Unlike free L-carnitine, acyl-L-carnitine is readily excreted into urine, thereby resulting in L-carnitine deficiency. Moreover, even with total carnitine concentration in blood within the normal range, the relative amount of free L-carnitine decreases due to the increase of acyl-L-carnitine. The administration of L-carnitine to such pediatric patients results in enhancement of the conversion of acyl CoA, such as propionyl CoA, deposited in blood into acyl-L-carnitine. Hence the recovery of mitochbndrial function is observed due to the excretion of toxic propionyl group and the increase in free CoA. Thus the administration of L-carnitine has therapeutic efficacy.

As L-carnitine is involved in metabolism of fatty acid in mitochondria and is regarded as an indispensable component of energy production, diverse research has been conducted. When L-carnitine is used as an additive for food or a beverage such as sports drink, it is disclosed that the efficient energy transduction of the fat stored in the body consequently results in the prevention of obesity or in stamina enhancement while engaging in sports activities.

Alternatively, in neonates, most of the desired amount of L-carnitine must be supplemented through mother's milk or artificial nourishment due to immature endogenous L-carnitine synthesis. However, therapeutic milk for the pediatric patients with metabolic disorders, which includes an amino acid mixture powder as the main ingredient, contains an extremely low level of L-carnitine. It is reported that when patients are nursed with such therapeutic milk, negative effect on normal development is observed.

Natural carnitine is levorotatory L-carnitine; and dextrarotatory D-carnitine is not present in natural substances. D-carnitine is regarded to be toxic because of its antagonistic inhibition against L-carnitine. Actually the adverse action due to the administration of racemate of carnitine, a mixture of L-carnitine and D-carnitine, for a longer period is also observed.

Carnitine can be produced synthetically. However, because carnitine obtained by chemical synthesis is racemic, purification processes of carnitine including optical resolution are required upon completion of the synthetic reaction, in order to remove toxic D-carnitine and to recover L-carnitine only. The synthetic method is disadvantageous in the view of the rather complicated manufacturing process, resulting in costly products and the possible risk of contamination with toxic D-carnitine due to insufficient purification.

Other biochemical methods have been developed for producing L-carnitine by means of using chemically synthesized dehydrocarnitine or apocarnitine as source materials with enzymes derived from microorganisms. However, these methods also indicate various disadvantages such as difficulty in purification methods of L-carnitine from the reactants, costly source materials, and no assurance of the safety of source materials. In addition, another attempt has been made to produce L-carnitine using fermentation by microorganisms, but it is not considered to be practical because of its low yield of L-carnitine.

Alternatively, some foods are known to be sources of L-carnitine. For example, milk such as cow's milk has been conventionally indicated to be a source for natural L-carnitine, but the content of L-carnitine in cow's milk is at about 20 $\mu$mol/100 g and regarded as considerably low. On the other hand, meat and fish contain relatively higher levels of L-carnitine. For example, beef, which is a source of higher level of L-carnitine, contains L-cartinine at about 800 mol/100 g. However there are disadvantages of a peculiar flavor or odor and difficulties in handling with respect to color or physical properties. Thus, it is significant that without modification, all of these methods have limited utilities and are considered impractical.

As for methods of producing L-carnitine from milk or modified milk products of mammals as the starting material disclosed in Japanese Patent Publication Sho62-63553 Public Bulletin is the method comprising the process of: using a byproduct (permeate) separated in the process of ultrafiltration of milk or modified milk products for starting material; desalting by means of electrodialysis; conducting column chromatography to absorb L-carnitine while passing through a column packed with strong acidic cationic ion-exchange resin; washing the column; and eluting to isolate L-carnitine. In this disclosure, it is described that lactose is preferably crystallized to precipitate for its removal before the desalting treatment. Further, as L-carnitine isolated by column chromatography is remarkably hygroscopic in powder form, it is preferable to disperse the concentrate onto lactose and use it as a triturated powder for practical use. Although the L-carnitine agent can be produced in this method, the efficiency of the entire process is not always regarded as desirable since the same lactose once removed in the processes is used again for trituration.

Furthermore, when the L-carnitine content in the resulting carnitine agent produced is 0.1 mmol/100 g or less, it is not considered to be practical because the daily dose for administration of the L-carnitine agent to introduce sufficient physiological effects becomes too high. On the other hand, when the L-carnitine content exceeds 100 mmol/100 g, more complicated manufacturing processes are required and the yield of L-carnitine decreases; this is economically inefficient. Additionally when the lactose content is 20 g/100 g or less, the function of lactose as filler is not sufficient, while a lactose content of 95 g/100 g or more makes it difficult to recover sufficient L-carnitine content. In addition, when ash content is 5 g/100 g or more, the agent tends to be hygroscopic with less fluidity.

As set forth, L-carnitine has an indispensable function in the body and also is useful material for pharmaceutical agents or food and drink. Therefore, it is advantageous to develop the method of producing the L-carnitine agent in a simple and effective manner, wherein the L-carnitine agent is: simple to handle; at higher concentrations and uniform in quality; economical; superior in safety; not only a highly concentrated form of L-carnitine but also containing a suitable filler; and useful as an additive for food or pharmaceutical agents without any modification.

SUMMARY OF THE INVENTION

An object of the present invention is to provide an L-carnitine agent that is simple to handle and superior in safety by means of using milk or modified milk products of mammals as a starting material, and the method for producing said agent.

As the result of extensive research to solve the above problems, the inventors discovered an efficient method for concentration of L-carnitine comprising: removing casein such as whey and so forth from milk or modified milk products of mammals to prepare the starting material; desalting treatment by means of electrodialysis, ion-exchange resin, nano-membrane filter and so forth; and partial removal of lactose by crystallization. Further, by subjecting the resulting L-carnitine to drying, the present invention has accomplished to establish the method of producing a L-carnitine agent that is simple in handling and superior in safety wherein said L-carnitine agent contains L-carnitine and lactose as useful filler with low ash content.

The present invention may include, but is not limited to, the following embodiments.

Milk of mammals used in the present invention is normally derived from, but not limited to, cows or goats because of the large scale of production. As for milk of mammals, not only raw milk, but a various kinds of milk such as skim milk, whole powdered milk, skim powdered milk and so forth may be used.

And also for modified milk products of mammals used in the present invention, whey, whey powder processed by drying whey, a byproduct (permeate) collected in the process of manufacturing the whey protein concentrate, permeate powder, a substance obtained by removing milk protein such as casein or whey protein and so forth from milk by filtering through a membrane or ion-exchange resin and the powder form thereof, and milk treated with enzyme and the powder form thereof, may be used.

In the present invention, milk or modified milk products of mammals, from which the above-described casein is removed, is used as a starting material.

Furthermore, casein can be precipitated by adjusting the pH or treated with an enzyme in advance, then isolated to remove it from milk.

The foregoing starting material is concentrated and adjusted to a solid content of 20~35% as desired, followed by adjusting the electrical conductivity to 0.1~5 mS/cm by means of desalting.

Desalting treatment may be performed by means of electrodialysis, ion-exchange resin, nano-membrane filter and so forth, preferably by electrodialysis in due consideration of the productivity in L-carnitine yield. For electrodialysis, the temperature during the desalting process is maintained at 4~50° C. and the electrical conductivity is adjusted to 1~5mS/cm. When using ion-exchange resin, both cationic ion-exchange resin and anionic ion-exchange resin are employed and the temperature is maintained at 4~40° C. throughout the desalting process and the electrical conductivity is adjusted to 0.1~5mS/cm. Although the type of ion-exchange resin is not particularly limited, strong acidic resin for cationic ion-exchange resin, and strong basic or medium basic resin for anionic ion-exchange resin is used, preferably with a ratio of cationic ion-exchange resin and anionic ion-exchange resin of 1:0.75~1.5 (by volume). In use of nano-membrane filter, temperature is maintained at 4~50° C. during desalting process and the electrical conductivity is adjusted to 0.1~5 mS/cm. Although the type of nano-membrane filter to be used is not particularly limited, it is preferable to use those having a sodium chloride rejection of 90% or less and an operating pressure of 5 Mpa or less.

To remove whey protein, water is added in advance to adjust the solid content to 6~20%, followed by ultrafiltration to collect filtrate (permeate), resulting in removing whey protein, a macromolecule component, from milk. An L-carnitine agent from which whey protein is substantially removed by the above treatments is especially useful as a pharmaceutical agent for food and drink for patients with protein metabolism disorders or milk allergy, for example, who are ought to avoid ingestion of milk protein.

After sterilizing the resulting solution, the solution is concentrated to adjust the solid content to 60% or more, and cooled with gentle agitation to crystallize lactose. The resulting lactose crystals are then separated and removed from the solution to produce a mother liquor of lactose. Through the above treatments, lactose is partially removed. Moreover, the above treatments for desalting and partial lactose removal may be conducted in any sequence. Therefore, the process can be started with desalting followed by partial lactose removal, or with partial lactose removal followed by desalting. In addition, the treatment for whey protein removal as described above can be performed as desired.

According to the present invention, the lactose content in the resulting L-carnitine agent may be adjusted as desired, by repeating the series of processes including the treatment of desalting and partial lactose removal. Even though only a part of lactose is removed through this process, approximately the entire amount of L-carnitine in the solution is recovered. Thus the lactose content of the resulting L-carnitine agent can be adjusted by choosing the frequency of repetition of the treatments. For example, to produce an L-carnitine agent with a higher lactose content, the frequency of repetition may be reduced. On the contrary, in order to produce an L-carnitine agent with a lower lactose content, indicative of higher purity of L-carnitine, the frequency of repetition of the treatment may be increased.

The resulting solution of the foregoing process contains abundant L-carnitine, an amount of lactose adjustable as desired, and a low content of ash due to the desalting treatment in the process. After this solution is appropriately concentrated with a conventional method, the concentrate is subjected to drying, for example, by means of a dryer such as an atomizer type or spray type and so forth to produce the L-carnitine agent.

An L-carnitine agent produced in accordance with the present invention may preferably have the composition comprising L-carnitine for 0.1~100 mmol/100 g, lactose of 20~95 g/100 g, and ash of 5 g/100 g or less. Furthermore, when milk or modified milk products of mammals is used as the starting material for the present invention, the resulting L-carnitine agent shows superior safety without containing any toxic D-carnitine.

DETAILED DESCRIPTION OF THE PREFERRED EMBODIMENT

According to the present invention, a preferable composition of an L-carnitine agent with lower ash content comprising L-carnitine with lactose as useful filler may be provided from milk or modified milk products of mammals as described above.

Because an L-carnitine agent of the present invention contains lactose as a useful filler as described above, it can easily be formulated in granular form which exhibits high solubility, by using a conventional Glad type granulator and also easily be formulated in tablet form with a tablet machine. During the formulation process, ingredients for additional physiological effects or drug efficacy may be combined concurrently with the L-carnitine agent. Even though these other ingredients are normally difficult to formulate in granular form or tablet form, the above formulation process can readily be accomplished. Additionally, the L-carnitine agent of the invention is characterized by features including simple handling such as low absorbency due to its lower ash content resulting from the desalting treatment and excellent fluidity and so forth, indicating that the agent is advantageous especially when combined concurrently with other ingredients. Furthermore, because the starting material for the present invention is milk or modified milk products of mammals, the resulting L-carnitine agent achieves superior safety without containing any toxic D-carnitine and excellent utility for manufacturing pharmaceutical agents or food and drink.

Due to the above advantageous features, the L-carnitine agent of the present invention is advantageous especially when combined with pharmaceutical agents or food and drink without any modification. Also, because the starting material for the L-carnitine agent of the present invention is milk or modified milk products of mammals, there is no disadvantage of odor such as noted with an L-carnitine agent derived from beef, and thus it is especially useful as an additive for food and drink. Furthermore, L-carnitine agent of the present invention, wherefrom whey protein is substantially removed, has a utility for manufacturing pharmaceutical agents or food and drink appropriate for administration to patients with a protein metabolism disorder or milk allergy ailment wherein the ingestion of milk protein is contraindicated, and thus it is proved to be significantly useful. Finally, the method of producing the L-carnitine agent in accordance with the present invention provides a safe L-carnitine agent from milk or modified milk products of mammals economically and efficiently, and thus it has an outstanding utility.

The following examples will serve to further illustrate the embodiment of the present invention. In the examples, each component was analyzed according to the following method.

L-carnitine was analyzed according to the following method. L-carnitine agent was dissolved in pure water to prepare a 10~20% (w/v) solution. To 100 ml of said solution, 200 ml of 1M disodium phosphate was added followed by 100 ml of 2.0N potassium hydroxide. After incubating said solution at 37° C. for 1 hour, it was neutralized with 1.0N chloride to provide the sample for L-carnitine analysis. The amount of free L-carnitine in the sample was determined by the method described by Kuragaki et al. (*Nihon Rinsho*, 91:2665, 1992) and the content of L-carnitine was calculated.

Lactose content was determined according to the following method. 1.0 g of L-carnitine agent was dissolved in pure water to prepare 100 ml solution. 20 $\mu$l of said solution was analyzed by means of high performance liquid chromatography (880-PU, manufactured by Nippon Bunko Co.Ltd.) equipped, with a differential refractometer (RI 71, manufactured by Showa Denko Co.Ltd.). In comparison with the measurement to the chromatogram of the standard lactose solution, the lactose content in the sample was calculated.

Further, the column used was LiChrospher $NH_2$ (manufactured by Merk), the mobile phase was the solution wherein the ratio of acetonitrile to water was 70:30(v/v). The analysis was performed at room temperature at a flow rate of 1.0 ml/sec.

A ash content was determined according to the following method. 1.0 g of the L-carnitine agent was weighed and placed in a porcelain crucible, maintained at 250° C. for 1 hour in an electric furnace, followed by additional heating at 550° C. for 1 hour to complete the ashing. After completion of the process, the crucible was weighed to calculate the weight of the contents, and ash content was determined therefrom.

EXAMPLE 1

60 kg of cow's milk was reacted with rennet for fractional precipitation of casein, resulting in 53 kg (solid content 6%) of whey was obtained. The resulting whey was concentrated to a solid content of 28% as measured with a thin-film descending type condenser (manufactured by Vhiegand, hereinafter the same). The concentrated whey solution was subjected to electrodialysis (manufactured by Ionix, hereinafter the same) for desalting, and the liquid was maintained at 40° C. until an electrical conductivity of 5 mS/cm was attained, and as a result, 10 kg of desalted whey was produced. After adjusting the pH to 6.5, the whey was sterilized at a high temperature for a short period of time, then concentrated to a solid content of 62% with a thin-film descending type condenser. The concentrated solution was gradually cooled with agitation, and incubated overnight at 5° C. to crystallize lactose. The crystallized lactose was removed by filtration to produce 5 kg of first lactose mother liquor (solid content 24%). The resulting first lactose mother liquor was again subjected to electrodialysis for desalting, maintained the liquid at a temperature of 40° C. until an electrical conductivity of 5 mS/cm was attained, and as a result, 4 kg of desalted lactose mother liquor was produced. After being sterilized at a high temperature for a short period of time, the mother liquor was concentrated to a solid content of 64% with the thin-film descending type condenser. The concentrated solution was gradually cooled with agitation and incubated overnight at 5° C. to crystallize lactose. The crystallized lactose was removed by filtration to produce 2 kg of second lactose mother liquor. Finally, the resulting second mother liquor was subjected to high-temperature sterilization for a short period of time, followed by condensation with the thin-film descending type condenser, then subjected pray-drying by means of a centrifuge atomizer type dryer (manufactured by Anhydro, hereinafter the same). As a result, 490 g of L-carnitine agent was produced.

The resulting L-carnitine agent contained 2.5 mmol L-carnitine, 62 g of lactose and 1.1 g of ash per 100 g, respectively.

EXAMPLE 2

In the same manner as described in example 1, 5 kg (solid content 24%) of first lactose mother liquor was produced from 60 kg of cow's milk. The resulting lactose mother liquor was processed with 100 ml of cationic ion-exchange resin (Amberlite IR120, strong acidic resin, manufactured by Dow Chemical) and 110 ml of anionic ion-exchange resin (Amberlite IRA410, strong basic resin, manufactured by Dow Chemical) for desalting to produce 5 kg of the desalted lactose mother liquor. After being sterilized at a high temperature for a short period of time, the desalted solution was concentrated to a solid content of 65% with a thin-film descending type condenser, gradually cooled with agitation and incubated for overnight at 10° C. to crystallize lactose. The crystallized lactose was removed by filtration to produce 2 kg of second lactose mother liquor. Finally, the resulting mother liquor was subjected to high-temperature sterilization for a short period of time, concentrated with the thin-film descending type condenser, then subjected to spray-drying by means of a centrifuge atomizer type dryer. As a result, 480 g of L-carnitine agent was produced.

The resulting L-carnitine agent contained 2.2 mmol L-carnitine, 67 g of lactose, and 0.8 g of ash per 100 g, respectively.

EXAMPLE 3

In the same manner as described in example 1, 20 kg of desalted whey (solid content 29%) was produced from 120 kg of cow's milk. After adjusting the pH to 6.5, water was added to the desalted whey to adjust the solid content to 12%. Then it was subjected to ultrafiltration through an ultrafiltration membrane (cut-off molecular weight 5 kDa, manufactured by DDS) and as a result, 44 kg of whey (solid content 10%) from which every protein had been removed was produced by recovering the filtrate (permeate). After being sterilized at a high temperature for a short period of time, the filtrate was concentrated to a solid content of 65% with a thin-film descending type condenser. Further, the concentrated solution was gradually cooled with agitation and incubated overnight at 8° C. to crystallize lactose. The crystallized lactose was removed by filtration to produce 7.2 kg of first lactose mother liquor (solid content 24%). The resulting lactose mother liquor was again subjected to electrodialysis for desalting, maintained at a temperature of 30° C. until an electrical conductivity of 0.7 mS/cm was attained, and as a result, 4.4 kg of desalted lactose mother liquor was produced. The resulting solution was subjected to high-temperature sterilization for a short period of time, followed by condensation to a solid content of 65%, gradually cooled with agitation, and maintained overnight at 8° C. to crystallize lactose. The crystallized lactose was removed by filtration to produce 2 kg of second lactose mother liquor. Finally, the resulting second lactose mother liquor was subjected to high-temperature sterilization for a short period of time, concentrated with the thin-film descending type condenser, then subjected to spray drying by means of a centrifuge atomizer type dryer. As a result, 700 g of L-carnitine agent was produced.

The resulting L-carnitine agent contained 3.7 mmol L-carnitine, 90 g of lactose, and 0.7 g of ash per 100 g, respectively.

EXAMPLE 4

In the same manner as described in Example 3, 30 kg of second lactose mother liquor was produced from 1800 kg of cow's milk. This second lactose mother liquor was again subjected to electrodialysis for desalting, maintained at a temperature of 30° C. until a electrical conductivity of 0.7 mS/cm was attained. The resulting solution was subjected to high-temperature sterilization, concentrated to a solid content of 65%, gradually cooled with agitation and incubated overnight at 8° C. to crystallize lactose. The crystallized lactose was removed by filtration to produce third lactose mother liquor. Furthermore, in the same manner, a series of processes including desalting with electrodialysis and partial removal of lactose was repeated twice, and produced the final resulting fifth lactose mother liquor. After the final lactose mother liquor was subjected to high-temperature sterilization for a short.period of time, concentrated with a thin-film descending type condenser, then subjected to spray-drying by means of a centrifuge atomizer type dryer. As a result, 600 g of L-carnitine agent was produced.

The resulting L-carnitine agent contained 62 mmol L-carnitine, 83 g of lactose, and 0.6 g of ash per 100 g respectively.

EXAMPLE 5

60 kg of cow's milk was reacted with rennet for fractional precipitation of casein to produce 53 kg (solid content 6%) of whey. The resulting whey was concentrated to a solid content of 28% with a thin-film descending type condenser, then processed through a nano-filter membrane (manufactured by Nitto Deriko, NTR-7250, hereinafter the same) under an operating pressure of 1.5 MPs at a temperature of 30° C. until an electrical conductivity of 5mS/cm was attained. As a result, 10 kg of desalted whey (solid content 29%) was produced. After adjusting the pH of the solution to 6.5, it was sterilized at a high temperature for a short period of time, concentrated to a solid content of 65%, gradually cooled with agitation and incubated overnight at 5° C. to crystallize lactose. The crystallized lactose was removed by filtration and as a result, 5 kg (solid content 23%) of first lactose mother liquor was produced. The resulting lactose mother liquor was again processed through the nano-filter membrane under an operating pressure of 1.5 MPs, maintained at a temperature of 30° C. until an electrical conductivity of 1 mS/cm was attained, and as a result, 4 kg of the desalted lactose mother liquor was produced. Furthermore, after being sterilized at a high temperature for a short period of time, the liquor was concentrated to a solid content of 64%, gradually cooled with agitation and incubated overnight at 8° C. to crystallize lactose. The crystallized lactose was removed by filtration and as a result, 1 kg of second lactose mother liquor was produced. The resultant was subjected to high-temperature sterilization for a short period of time, concentrated with the thin-film descending type condenser, then subjected to spray-drying by means of a centrifuge atomizer type dryer. As a result, 500 g of L-carnitine agent was produced.

The resulting L-carnitine agent contained 1.2 mmol L-carnitine, 58 g of lactose, and 1.4 g of ash, respectively.

THE EFFECT OF THE INVENTION

The present invention provides an L-carnitine agent wherein the starting material is milk or modified milk products of mammals, and the method of-producing the agent. The method of producing L-carnitine in accordance with the present invention is advantageous to produce a safe L-carnitine agent economically and efficiently, thus providing excellent utility.

Because the L-carnitine agent of the invention uses milk, a natural substance, as a starting material, toxic D-carnitine is not present, and superior safety is attained. Furthermore, the L-carnitine agent of the invention has advantageous characteristic features of simple handling including outstanding utility when the agent is combined with pharmaceutical agents or food and drink, because the agent contains lactose useful as a filler, and has low absorbency due to a low ash content, and excellent fluidity, for example.

The L-carnitine agent of the present invention with the above characteristic features can be utilized by combining it with pharmaceutical agents and food or drink without any modification, thus attaining excellent utility. Also, because the L-carnitine agent of the present invention is produced from milk, it doesn't have any disadvantage of a peculiar odor such as that noted with the L-carnitine agent derived from beef, and thus it is a preferable source as an additive for food and drink.

The L-carnitine agent of the present invention wherein whey protein is substantially removed from milk is especially useful for manufacturing pharmaceutical agents or food and drink to administer to patients with a protein metabolism disorder or milk allergy, etc. wherein the ingestion of milk protein is contraindicated.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of producing an L-carnitine agent, characterized by adjusting:

an L-carnitine content to 0.1–100 mmol/100 g;

a lactose content to 20–95 g/100 g; and an ash content to 5 g/100 g or less, respectively, by (i) subjecting milk or modified milk products of mammals from which casein is removed, to the treatment of desalting and partial removal of lactose, (ii) repeating step (i) multiple times to increase the L-carnitine content, thereby obtaining an L-carnitine solution, and (iii) drying the solution, thereby obtaining said L-carnitine agent.

2. The method set forth in claim 1, characterized by adjusting the electrical conductivity to 0.1~5 mS/cm by desalting treatment.

3. The method set forth in claim 1, characterized by using a means selected from the group consisting of an electrodialyser, ion-exchange resin, and nano-filter membrane.

4. The method set forth in claim 1, characterized by further comprising the treatment of removing whey protein.

5. The method set forth in claim 2, characterized by using a means selected from the group consisting of an electrodialyser, ion-exchange resin, and nano-filter membrane.

6. The method set forth in claim 2, characterized by further comprising the treatment of removing whey protein.

7. The method set forth in claim 3, characterized by further comprising the treatment of removing whey protein.

* * * * *